(12) United States Patent
Chaput et al.

(10) Patent No.: US 8,901,185 B2
(45) Date of Patent: Dec. 2, 2014

(54) HYBRID ORGANIC-INORGANIC MATERIAL CONSTITUTED BY A SILICA NETWORK HAVING PHOTOCHROMIC AGENTS AND OPTICAL POWER LIMITING AGENTS AS A DOPING AGENT IN THE MATERIAL

(75) Inventors: Frédéric Chaput, Villeurbanne (FR); Stéphane Parola, Jonage (FR); César Lopes, Linkoping (SE); Denis Chateau, Caluire et Cuire (FR); Cédric Desroches, Lyons (FR)

(73) Assignees: Universite Claude Bernard Lyon I, Villeurbanne Cedex (FR); Centre National de la Recherche Scientifique, Paris Cedex (FR); FOI Swedish Defence Research Agency, Stockholm (SE)

( * ) Notice: Subject to any disclaimer, the term of this patent is extended or adjusted under 35 U.S.C. 154(b) by 0 days.

(21) Appl. No.: 13/638,778

(22) PCT Filed: Apr. 12, 2011

(86) PCT No.: PCT/EP2011/055720
§ 371 (c)(1),
(2), (4) Date: Dec. 14, 2012

(87) PCT Pub. No.: WO2011/128338
PCT Pub. Date: Oct. 20, 2011

(65) Prior Publication Data
US 2013/0131203 A1 May 23, 2013

(30) Foreign Application Priority Data
Apr. 12, 2010 (EP) ..................... 10305377

(51) Int. Cl.

| | | |
|---|---|---|
| C08L 83/00 | (2006.01) | |
| C03C 14/00 | (2006.01) | |
| C03B 19/12 | (2006.01) | |
| C01B 33/158 | (2006.01) | |
| C01B 33/16 | (2006.01) | |
| C01B 33/157 | (2006.01) | |
| C03C 1/00 | (2006.01) | |
| C01B 33/145 | (2006.01) | |
| C01B 33/146 | (2006.01) | |
| C01B 33/155 | (2006.01) | |
| C07F 7/21 | (2006.01) | |

(52) U.S. Cl.
CPC .............. *C08L 83/00* (2013.01); *C03C 2214/16* (2013.01); *C03C 2201/60* (2013.01); *C03C 14/008* (2013.01); *C03C 2203/32* (2013.01); *C03B 19/12* (2013.01); *C03C 2203/28* (2013.01); *C01B 33/158* (2013.01); *C01B 33/163* (2013.01); *C03C 2214/32* (2013.01); *C01B 33/157* (2013.01); *C03C 1/008* (2013.01); *C03C 2203/27* (2013.01); *C01B 33/145* (2013.01); *C03C 1/006* (2013.01); *C01B 33/146* (2013.01); *C01B 33/155* (2013.01); *C03C 14/006* (2013.01); *C07F 7/21* (2013.01); *C01B 33/16* (2013.01); *C03C 2214/17* (2013.01)
USPC ................ 521/85; 521/90; 521/154; 524/588

(58) Field of Classification Search
None
See application file for complete search history.

(56) References Cited

U.S. PATENT DOCUMENTS

| 4,851,150 | A * | 7/1989 | Hench et al. ................... 516/111 |
|---|---|---|---|
| 6,624,237 | B2 * | 9/2003 | Biteau et al. .................. 524/588 |
| 6,764,690 | B2 * | 7/2004 | Ahola et al. .................. 424/422 |
| 7,250,214 | B2 * | 7/2007 | Walter et al. .................. 428/405 |
| 2005/0244807 | A1 * | 11/2005 | Abbotto et al. .................... 435/4 |
| 2013/0131203 | A1 * | 5/2013 | Chaput et al. .................... 521/85 |

FOREIGN PATENT DOCUMENTS

| WO | 94/25406 | 11/1994 |
|---|---|---|
| WO | 00/35818 | 6/2000 |
| WO | 2004/092820 | 10/2004 |

OTHER PUBLICATIONS

Faloss et al. "Toward millions of laser pulses with pyrromethene- and perylene-doped xerogels" Applied Optice, 36(27), 1997, 6760-6763.*
Kim et al. "Organically Modified Silica Nanoparticles Co-encapsulating Photosensetizing Drug and Aggregation-Enhanced Two-Photon Absorbing Fluorescent Dye Aggreages for Two-Photon Photodynamic Therapy" J. Am. Chem. Soc. 2007, 129, 2669-2675.*
Yariv et al. "Laser properties of pyrromethene dyes in sol-gel glasses" Optical Materials, 13 (1999) 49-54.*
Zieba R. et al., "Preparation of . . . of light" Advanced Functional materials Wiley-VCH Verlag GMBH Germany, vol. 19, No. 2, pp. 235-241, XP007915768.
Parola S. et al., "Hybrid materials . . . limiting applications", Proceedings of the SPIE—The International Society for Optical Engineering SPIE—The International Society for Optical Engineering, USA, vol. 6401, pp. 64010D-1, 2006, XP007915769.

(Continued)

*Primary Examiner* — Robert S Loewe
(74) *Attorney, Agent, or Firm* — Clark & Brody

(57) ABSTRACT

The invention concerns a preparation process of a hybrid organic-inorganic material including the following successive steps:
a) preparation of a neutral organosilicon sol in at least one organic solvent,
b) incorporation of a doping agent into the neutral organosilconsol, and production of a doped sol,
c) incorporation into the doped sol, of an accelerating agent in order to activate the subsequent gelation of the sol,
d) condensation of the sol in order to obtain a crosslinked gel,
e) drying of the gel and production of a stable doped gel.
and the material obtainable by such a method.

9 Claims, No Drawings

(56) References Cited

OTHER PUBLICATIONS

Parola S. et al., "Hybrid materials . . . nonlinear absorption", Proceedings of the SPIE—The International Society for Optical Engineering SPIE—The International Society for Optical Engineering, USA, vol. 5934, pp. 593404-1, 2005, XP007915754.

Ortenblad M. et al., "Hybrid materials . . . Optical limiting", Organic/Inorganic Hybrid materials—2004. Materials Research Society Warrendale, PA, USA, 2005, pp. 405-410, XP007915770.

Database Compendex (online), Engineering Information, Inc., NY, USA, 2008, Desroches C. et al., "Hybrid Materials . . . Molecular Level", XP002610022, Database accession No. E201026130 41847 & Nonlinear Optics Quantum Optics, 2009, 2008, Old City Publishing USA, vol. 38, No. 3-4, 2008, pp. 259-269.

Desroches C. et al., "Design and . . . optical properties", Dalton Transactions May 21, 2003 Portland Press Ltd GB, No. 10, May 21, 2003, pp. 2085-2092, XP007915771.

Kim G-D et al., "Deffect of . . . Organic molecules", Journal of Sol-Gel Science and Technology, Springer, NY, USA, vol. 10, No. 3, Nov. 1, 1997, XP000721254, pp. 283-289.

Oh J. et al., "Direct depositions . . . alkoxide solution", Journal of non-Crystalline Solids, vol. 241, No. 2-3, pp. 91-97, Nov. 2, 1998, XP004158647.

\* cited by examiner

HYBRID ORGANIC-INORGANIC MATERIAL CONSTITUTED BY A SILICA NETWORK HAVING PHOTOCHROMIC AGENTS AND OPTICAL POWER LIMITING AGENTS AS A DOPING AGENT IN THE MATERIAL

FIELD OF THE INVENTION

The invention concerns the field of hybrid organic-inorganic materials. More precisely, the invention is related to a preparation process of hybrid materials by the sol-gel technique, and to hybrid materials containing molecular species the concentrations of which can be very high.

BACKGROUND ART

The preparation of inorganic glasses using low temperature routes (soft-chemistry) has been described as an extremely interesting alternative to conventional glass manufacturing. It is especially well appropriate for preparing hybrid matrices. These hybrid materials contain a mineral part which coexists with an organic part. The organic part helps synthesis of xerogels especially during the drying step. This approach has been known since several decades and intensive researches have been devoted in the field for the past 20 years. Another interest of the low temperature routes is that one can easily incorporate in the glassy matrix, thermally sensitive doping agent, such as functional molecular systems or nanomaterials which could confer multifunctionalities to the obtained hybrid material. The interactions between the hybrid matrix and the doping agent are controlled by the nature of the organic parts and their concentrations. The properties of the doped xerogel can be influenced by the strength of these interactions.

Silica based materials are suitable host matrices since they combine good thermal and mechanical properties. In addition, they exhibit interesting optical properties which can be used in many applications. So a large variety of materials for optical and optoelectronic applications were developed by trapping active species into the polymeric network of the silica based gels. Two methods for preparing guest-host systems using the sol-gel technique were developed. The first one consists in simply dispersing the active species in the matrix without strong interaction between the guest system and the silica backbone. In the second approach, the guest active units are strongly bonded to the silica network (Adv. Mater., 2003, 15(23), 1969). The main drawback of the first method is that the solubility of the guest system (organic or organometallic molecules, inorganic nanomaterials) is often low in the more or less polar $SiO_2$-based gels and xerogels. Hence, chemical covalent grafting of the molecular species to the silica backbone can be suitable for greatly increasing their concentrations in the range of 0.1-0.5 M or higher.

The bonding of the doping agent can be accomplished via tri-alkoxysilyl groups in the organic molecular framework, which are hydrolysed and subsequently co-condensed with the silicon alkoxide during the sol-gel process. In Adv. Funct. Mater. 2009, 19, 235-241, the inventors of the present invention described the preparation by sol-gel technique of glass materials from di(arylethylnyl)diphosphinePt(II) complexes functionalized with siloxane groups on the peripheral aromatic rings. Concomitantly the modification of the matrix using alkyl substituted alkoxides conferring hydrophobicity to the network can improve the compatibility between the two systems. Nevertheless, the grafting may induce structural changes on the functional doping agents. Moreover the chemistry of the doping agent remains complicated in most cases.

Another general technical problem, in both approaches, concerns the control of the drying step which has to be very slow to prevent the matrix from cracking. So, different solutions have been developed. One of them has proposed to use additives, such as formaldehyde, in order to control the ultrastructure of the gel solid and pore phases. Gelation, aging, drying, and densification of the sol-gel derived monoliths may be performed rapidly in tens of hours instead of tens of days without cracking (U.S. Pat. No. 4,851,150). However, this implies the contamination of the final materials as the result of the presence of by-products.

SUMMARY OF THE INVENTION

So, a purpose of the invention is to solve the above mentioned drawbacks of the prior art. In particular, the invention proposes a new process using the sol-gel technique that enables the preparation of hybrid monolithic materials with very high concentration of doping agent. The process according to the invention can also be transposed to the preparation of films, fibers or powders and can be adapted to both dispersed and grafted systems.

In this context, the present invention concerns a preparation process of a hybrid organic-inorganic material including the following successive steps:
 a) preparation of a neutral organosilicon sol in at least one organic solvent,
 b) incorporation of a doping agent into the neutral organosilicon sol, and production of a doped sol,
 c) incorporation into the doped sol, of an accelerating agent in order to activate the subsequent gelation of the sol,
 d) condensation of the sol in order to obtain a crosslinked gel,
 e) drying of the gel and production of a stable doped gel.

According to the invention, in view of the use of an accelerating agent, gelation must occur very quickly, for instance within a few seconds. Preferably, the gelation time (duration of step d)) must not exceed more than one hour. Thus the fast kinetics of condensation reactions leads to the rapid development of the percolating inorganic network. As a consequence, the step d) which leads to a solid state corresponds to a quick and pronounced condensation of the sol that leads to a highly crosslinked gel. So, a short gelation time, associated with a high condensation rate, "freezes" the distribution of the doping species and limits their aggregation even for highly concentrated sols.

Another object of the invention is related to a hybrid material constituted by a silica network in which at least one doping agent representing 30%, and preferably at least 40% in mass of the material, is included.

Another object of the invention is related to a hybrid material constituted by a silica network in which at least one doping agent which is quasi-insoluble is included. The final concentration of the doping agent in the matrix is much higher than the saturation concentration in the matrix prepared by a conventional process; a typical saturation concentration is about $10^{-5}$ mole/L.

The invention is also related to these materials obtainable by the preparation process according to the invention.

DETAILED DESCRIPTION OF THE INVENTION

For the purposes of this invention, the term "organo-silicon sol" refers to a hydrolysate of organoalkoxysilane monomer. The alkoxy groups of the organoalkoxysilane monomer, the formula (I) of which is described hereafter, are partially or totally hydrolyzed and transformed in silanol groups (Si—OH).

The "organo-silicon sol" is described as "neutral" because the free acid was eliminated or partially eliminated by washing or by adding a base in an appropriate concentration. In particular, the pH of the organo-silicon sol, when the doping agent is incorporated belongs to the range 6.5-7.5.

The term "doping agent" refers to functional entities that will confer specific properties to the material, such as optical, mechanical, catalytic or magnetic properties. Photochromic agents and optical power limiting agents are examples of such doping agents. The doping agents are chosen among organic, organo-metallic or inorganic molecular species, as well as among inorganic nanomaterials. The solubility of the organic or organo-metallic doping agents incorporated must be high enough in the solvent selected for the sol that is compatible with the sol. In some cases, supplementary quantities of solvent are introduced in the sol to completely dissolve the organic or organo-metallic doping agent. Increasing temperature of the sol can play the same role. Mixtures of doping agents can easily be achieved using this process, even if they present different solubilities.

The condensation rate Tc of the sol made of silicon species $T^1$, $T^2$ and $T^3$ (The superscript number 'n' in 'T$^n$' denotes the number of bridging oxygen (OSi) surrounding the silicon atom) can be defined by the following formula: Tc=[0.5(area $T^1$)+1.0(area $T^2$)+1.5(area $T^3$)]/1.5; area under peaks of species $T^n$ on $Si^{29}$ NMR spectra. In an advantageous variant of the process according to the invention, the organo-silicon sol obtained in step a) to which the doping agent is added has a great condensation rate equal to or greater than 0.65. In particular, this sol has a condensation rate in the range 0.75-0.95 and preferably between 0.75 and 0.85 or more preferably between 0.85 and 0.95. With such high condensation rate of the sol, the gelation is very fast and efficient. In such cases, the gelation which corresponds to a bodying up of the material leads to a very low increase of the condensation rate. Thus a less polar matrix is obtained. A low concentration of silanol groups increases the compatibility of the silica network with the doping agents. Moreover, the high concentration rate of the sol induces low water release during the final gelation and allows preparation of water free materials.

According to a first variant of the invention, the organo-silicon sol used in the invention is prepared according to WO 00/35818. In this case, the hydrolysis of an organo-silicon precursor is conducted with a large water excess. Then the hydrolysate is concentrated and left until a phase separation (an aqueous phase and an organo-silicon phase) appears. The sol corresponds to the collected and treated organo-silicon phase which exhibits very low water contents. Moreover the organo-silicon sol exhibits a high condensation rate, equal to or greater than 0.65. This sol can be dried more and dispersed again in a hydrophobic solvent. More precisely, the organo-silicon sol may be prepared as follows:

a1) hydrolysis of an initial volume Vsi of an alkoxide precursor containing at least an organo-silicon monomer precursor with formula:

$$R^1{}_n Si(OR^2)_{4-n} \quad\quad (I)$$

in which:
the groups $R^1$, identical or different, represent an alkyl group, an aryl group, a vinyl group or H,
the groups $R^2$, identical or different, represent H or an alkyl group, and n is equal to 1 or 2, and n=2 if one of the group $R^1$ represents H,
the Hydrolysis being performed with a water amount such as:

$$\frac{x\mathrm{H_2O}}{x\mathrm{Si}} \geq 8$$

(where $x\mathrm{H_2O}$ and $x\mathrm{Si}$ represent the number of moles of $\mathrm{H_2O}$ and Si respectively)

and, with a possible quantity of an organic solvent such that $$0 \leq \frac{x Solvent}{x\mathrm{Si}} \leq 8$$

(where $xSolvent$ represents the number of moles of solvent)

and under the condition that when:

$$\frac{x\mathrm{H_2O}}{x\mathrm{Si}} = 20,\ xSolvent = 0$$

to obtain a hydrolysate of the alkoxide precursor;
a2) concentration of the hydrolysate down to a volume substantially equal or lower to the initial volume Vsi (water and solvent evaporation);
a3) ageing the concentrated hydrolysate until a clear phase separation occurs; aqueous and organo-silicon phases obtained,
a4) collection of the organo-silicon phase and dispersion in a solvent,
a5) optional drying of the organo-silicon sol in solvent phase and optional exchange of the organic solvent by another, well adapted to have a stable and homogeneous doped sol when the doping agent will be incorporated.

According to one embodiment, it is used a monomer (I) in which $R^1$ represents a methyl, ethyl or phenyl group, or a substituted phenyl group, preferably substituted with one or several groups chosen between non-polar groups and the vinyl group; $R^2$ represents a ($C_1$-$C_7$)alkyl group; and n is 1 or 2, preferably 1 when none of the $R^1$ groups represents H.

Among the particularly preferred organo-silicon precursors with formula (I), the following can be mentioned: methyltrimethoxysilane (MTMOS), methyltriethoxysilane (MTEOS), ethyltriethoxysilane (ETEOS), d methyldimethoxysilane (DMDMOS), dimethyldiethoxysilane (DMDEOS), diethoxymethylsilane (HMDEOS), phenyltriethoxysilane (PTEOS) and vinyltriethoxysilane (VTEOS). In a preferred embodiment, the monomer precursor of formula (I) is selected among methyltriethoxysilane, ethyltriethoxysilane and their mixtures. WO 00/35818 can be consulted for more details.

According to a second variant of the invention, the highly condensed neutral organo-silicon sol is prepared by treating an organo-silicon sol prepared according to WO94/25 406, in order to neutralize the sol and increase its condensation rate. The treatment may be performed with neutral or basic aqueous solution or by heating the organo-silicon sol until a condensation rate higher than 0.5 is obtained. The condensation rate can be measured using NMR spectroscopy. As previously described, the organo-silicon phase obtained after treatment is collected and may be dispersed in an appropriate solvent. The obtained sol may be dried and dispersed again in a hydrophobic solvent, in order to obtain the usable sol for the rest of the process. In this second variant, as described in WO94/25 406, the hydrolysis of one or several organo-alkoxysilanes dissolved in an organic solvent or mixtures of organic solvents is performed, using an acidic aqueous solution with a pH equal to or smaller than 3. The sol is obtained by elimination of the organic solvent(s) and of the residual alcohols and concentration of the solution by distillation.

In a third variant of the invention to prepare a neutral organo-silicon sol with a high condensation rate and low water content, a mixture of a silicon alkoxide and an acidic aqueous solution with a pH smaller than 4 is heated at temperature higher than 60° C. The heating treatment promotes the hydrolysis as well as the condensation. Hydrolysis is performed with a water amount such as:

$$\frac{xH_2O}{xSi} \geq 6$$

(where $xH_2O$ and $xSi$ represent the number of moles of $H_2O$ and Si respectively)

and, with a possible quantity of an organic solvent such that $$0 \leq \frac{xSolvent}{xSi} \leq 8$$

(where $xSolvent$ represents the number of moles of solvent).

In the case where one alcohol is used as solvent, the more the alcohol content is high, the more the condensation rate is low (with identical temperature and time of treatment). In addition, in the case of solventless condition, the more the water content is low, the more the condensation rate is low (with identical temperature and time of treatment). Distillation of alcohol produced during the hydrolysis step reduces the heating treatment time for the same condensation rate. The organo-silicon phase can be isolated by removing the solvent under reduced pressure, until a very viscous sol is obtained. As previously described, the organo-silicon phase may be dispersed in an appropriate solvent. The obtained sol may be dried and dispersed again in an appropriate solvent, for instance a hydrophobic solvent, in order to obtain the usable sol.

The organo-silicon sol used in step b) may also be directly obtained in the suitable solvent or may be solubilized in at least one solvent selected, for instance, among ketones such as acetone or 2-butanone, tetrahydrofuran, chloroform, dichloromethane, amides such as DMF and their mixtures . . . . Advantageously, this solvent is selected so that the doped sol would be stable and homogeneous, without precipitation of the doping agent in the conditions of temperature and pressure selected for the implementation of the process. When the doping agent is an organic or organometallic one, the solvent will be selected so that the doping agent will be soluble into, in the conditions of temperature and pressure selected for the implementation of the process.

If necessary, the amount of water, oxygen and remaining organic solvents in the sol may be controlled. Advantageously, whatever the process used for the preparation of the neutral organo-silicon sol, its solid content (wt %) is higher than 20%. This characteristic of the sol contributes to reduce the shrinkage of the xerogel, to reduce the gelation time and to bring enough matter in order to encapsulate the doping agent.

It is interesting to reduce the water content rate when the doping agent is insoluble in water. In these cases, the amount of water of the neutral organo-silicon sol is, preferably, less than 1% in mass. In an alternative embodiment of the invention, it is used a neutral organo-silicon sol that is deprived of water, as determined by the absence of peaks corresponding to water by NMR $^1H$. When the content of water have to be reduced, whatever the process used for the preparation of the organo-silicon sol, the recovered organo-silicon phase is preferably subjected to a drying step above-mentioned (a5) in the first variant, either (1) by addition of a solvent with a boiling point above 100° C., at atmospheric pressure, or by addition of a solvent forming an azeotrope with water (for example 2-butanone with a boiling point of 79.6° C.) and evaporation of the solvent, or (2) by extraction with a hydrophobic solvent and using a drying agent (for example $MgSO_4$). The use of a solvent with a boiling point greater than 100° C., leading to treat the sol at relatively high temperature in order to eliminate the solvent, may have the disadvantage of changing the sol a lot (too high condensation rates, too early gelation). Azeotropic distillation, allows to lower temperatures, even after repeated distillations the water content in the sol remains relatively important. It is therefore preferable to dry by extraction with a hydrophobic solvent exhibiting a boiling point equal to or smaller than 80° C. The water elimination is improved by the addition of a drying agent like $MgSO_4$. Preferably, ethyl acetate or diethyl ether is used as solvent. The recommended drying method is diethyl ether extraction followed by a treatment with a drying agent. However, this implies removing the drying agent by filtration and replacing ether with another solvent. Indeed, diethyl ether is not a solvent appropriate for the subsequent use of the sol. The sol is rather polar and it is hardly soluble in diethyl ether. Diethyl ether can be replaced easily with any solvent with higher boiling point and in which organo-silicon species are highly soluble. Diethyl ether is therefore evaporated partially under reduced pressure (down to the solubility limit of the sol), the replacement solvent is added in excess (for example 2 Vsi), then the evaporation is carried on until the volume Vsi is obtained. This latter operation is, preferably, conducted twice in order to evaporate all the diethyl ether present in the sol.

In step b), one or several doping agents are added to the sol. Advantageously, the doping agent(s) used in the invention do(es) not correspond to a doping agent functionalized with siloxane groups as described in Adv. Funct. Mater. 2009, supra. Their quantities are selected in order to reach the required concentrations in the final material. The solvent is selected based on its compatibility with the doping agent. The solvent is chosen in order to obtain a doping sol which is stable and homogeneous, without precipitation. The inserted doping agents are rather organophilic but a selected solvent for the sol broadens the nature of these doping agents. Advantageously, the solvent will be selected for its miscibility with the sol. When the doping agent is organic or organometallic, it will preferably be soluble in the solvent. It is possible to add a solvent or to replace the initial solvent by another one, in order to enhance the solubility of the doping agents in the sol. The sol and the doping agent(s) are mixed together. The resulting mixture is stirred until the doped sol is transparent. The temperature and the pressure can also be increased in order to enhance the solubility of the doping agent. For instance, a temperature in the range of 30 and 200° C. and a pressure in the range of $P_{atm}$ and 200 bars can be used. The temperature and the pressure would be selected in order to obtain a transparent sol after stirring. According to the invention, the doped sol can be characterized by a high concentration of doping agent, defined as equal or higher than 0.7 mole/L (of sol).

The doped sol obtained is stable and homogeneous, without precipitation of the doping agent. According to the invention, the doping agent may present variable properties. The doping agents can be weakly polar, hydrophobic or hydrophilic.

Organic or organo-metallic molecules such as Pyrromethene597, 1,4,8,11,15,18,22,25-octabutoxphtalocyanine, 2,11,20,29-tetra-tert-butyl-2,3-naphtalocyanine, platinium complexes such as acetylides, naphtalocianines, lanthanide complexes, such as europium complexes, metal or metallic oxide nanoparticles (Ag, Au) are particularly interesting. In a particular embodiment, the doping agent(s) included in the obtained hybrid material is (are) preferably chosen to confer optical power limiting properties to the material. For instance, the doping agents can be chosen between: Platinum(II) complexes or naphtalocianines. Acetylides are examples of Platinum(II) complexes that can be used. So, in these cases, the materials obtained are non linear optical materials and are, for instance, useful for the protection of optical sensors against laser aggressions. For catalysis applications, metal (Ni, Co, Pt or Pd, for instance) or oxide ($TiO_2$ for instance) nanoparticles can be incorporated in the materials.

The incorporation of the accelerating agent in the doped sol is rapidly achieved, after the doping agent is completely dissolved in the sol. For instance, the accelerating agent is included, less than 1 hour after the introduction of the doping agent(s). The accelerating agent is basic and will allow a fast condensation of the network during subsequent step d). The accelerating agent may, for example, be selected among 2-(trimethoxysilyl)-ethyl-2-pyridine, trimethoxysilylpropyldiethylenetriamine, N-(2-aminoethyl)-3-aminopropyltrimethoxysilane, 3-aminopropylmethyl-diethoxysilane, 3-aminopropyltriethoxysilane (APTES),3-isocyanatopropyltriethoxysilane, 3-thiocyanatopropyltriethoxysilane, aminophenyltrimethoxysilane, N-methylaminopropyltrimethoxysilane, 3-(2-imidazolin-1-yl)propyltriethoxysilane, diethylamine, triethylamine, diethanolamine, monoethanolamine, dodecylamine, aminopropyltrimethoxysilane (APTMS), N-methylAPTMS, N,N-dimethylAPTMS and N-methylpyrrolidone. The amount of accelerating agent will be high enough for reaching the desired cross-linked rate of the gel before drying and elimination of the solvent(s). In particular, the concentration of the accelerating agent incorporated in step c) will be in the range 0.02 mM-1 mM, for instance around 0.2 mM. The concentration of the accelerating agent preferably corresponds to a molar ratio accelerating/silicium in the range 0.002-0.2.For instance, the amount of accelerating agent should be higher than 2µl per gram of sol when the solid content is higher than 30%.

According to the invention, the accelerating agent may also be chosen among the triggered bases like the thermobases and the photobases (Polycat SA1/10, molecule with oxime-urethane groups).

Whereas the process described in WO 2004/092820, the process according to the invention can be prosecuted without carbazole derivatives and so, the obtained hybrid organic-inorganic material doesn't contain any carbazole derivative.

When both the doping agent and the accelerating agent are present in the sol, the gelation occurs instantaneously. This gelation takes place by condensation of the remaining silanol groups present in the sol. For instance, the gelation is carried at a temperature belonging to the range 20-100° C., preferably to the range 70-80° C. In particular, the gelation can be carried at a temperature in the range 20-50° C., for instance at room temperature (20-25° C.) or at a temperature slightly above room temperature (30-50° C.). Preferably, the gelation is carried at a temperature below the temperature used during the subsequent drying step. Most of the time, the sol is poured into a mould under or without heating, for gelation. Advantageously, the gelation can be carried out in a closed vessel to prevent solvent evaporation. The use of a heating improves the solubility of the doping agent but the temperature has to be controlled in order to avoid or minimize the elimination of solvent during gelation. Preferably, the gelation is carried out without elimination of solvent or with a slight elimination corresponding to less than 5% of the solvent(s) present before the addition of the accelerating agent.

The aging step corresponding to the gelation is very quick and may take only few minutes, for instance less than ten minutes or less than one hour, that is considerably shorter than conventional techniques which generally require several days. According to the invention, the use of a rapid addition of the accelerating agent induces an ultrafast condensation which freezes the material and blocks the doping agent diffusion before the drying step and the removal of the solvent(s). According to the invention, the solvent(s) which is(are) present (especially the organic solvent of the sol) is(are) preferably removed after this gelling step d). The solvent(s) is(are) removed during the drying step e) and not during the gelling step whereas in the processes described in the prior art (WO 94/25 406, WO 00/35 818, Zieba R. et al. Advanced Functional Materials 19, 2, 2009, 235, Parola S. et al. Proceeding of the spie—the international Society for Optical Engineering spie—the international society for optical engineering US—vol 6401, 2006, pages 64010D-1 and vol 5934, 2005, pages 593404-1) where the gelation occurred in the slow drying process within several days.

In a last step, the resulted material is dried. For instance a drying, at a temperature between 80° C. and a temperature below the decomposition of the doping agent (typically 200° C.), during 1 to 48 hours, can be carried on.

In the process according to the invention, the solvent is important because it is not removed before gelation (unlike processes, previously described). Gelation occurs within minutes or even within seconds, for instance at room temperature (or temperature slightly above room temperature) after the adding of a given amount of the agent which accelerates the condensation (amino-alkoxysilane, for example). In this step, the distribution of doping agents is frozen. The mobility of the doping agents is excessively reduced, and, as result, the precipitation of dopants will be avoided during the aging step. The network of the highly crosslinked gel efficiently isolates the molecules of doping agents from each other. Subsequently, the solvent is removed from the gel during a drying step generally in an oven, and preferably at a temperature higher than the gelling temperature. Drying takes several hours for small samples and a few days for large samples. Removal of solvents does not alter the distribution of doping agents because they are strongly trapped in the polymer network. The doping agents concentration in the xerogel can be extremely important. The gel can be obtained in a mould made of polypropylene. The filled mould is subsequently placed in an oven, in order to achieve the drying of the gel.

The obtained hybrid material is functionalized with one or several doping agents. The process according to the invention allows the inclusion of a very high concentration of doping agents. In particular, the concentration of doping agents can be superior to 30% in mass, preferably 40% in mass for the optical limiting application. The invention allows the preparation of material with extremely high payloads of doping agents, controlling the dispersion without any aggregation. The doping agent is uniformly distributed in the material. The homogeneity of the material is evidenced by using spectroscopic methods and thermal analysis, DSC for example). In some cases, the doping agent(s) may represent up to 50% in mass of the material. The process according to the invention avoids the precipitation of the doping agent even with high concentrations of doping agent.

The hybrid materials prepared according to the invention are highly homogeneous and can be shaped as porous or dense monoliths, films and powders. The interaction between the host agents can be easily tuned controlling the concentration and the fast condensation and no interaction can be obtained if necessary even at high payloads. Concentrations over 50% in mass can thus be prepared with a homogeneous dispersion of the doping agent, and no other method is available for the preparation of such materials. There is no limit of concentrations according to the invention, even with species showing very low solubility in solvent. Indeed the process can occur at temperature and pressure allowing dissolution of the doping agent (increasing the solubility constant) using closed vessels and the instantaneous condensation allow to gelified the matrix with homogeneous dispersion of the doping agent. So, concentrations up to 4 times more than in saturated liquids in normal conditions of temperature and pressure can be reached. After cooling the dispersion is then preserved in the final solid since the doping agent cannot move anymore in the matrix.

The hybrid materials according to the invention can be obtained as massive monolith materials such as xerogels or aerogels or as thin films. The applications of the materials are various and depend on the nature of the incorporated doping agent. Application in optical limiting devices (protection against lasers) or other optical devices (lenses, windows, glasses, lasers, sensors, memories . . . ), or in catalysts supports can be cited.

The following examples illustrate the invention.

Example 1

This example describes the general procedure used to prepare an organo-silicon sol with high condensation rate and low water content. The hydrolysis is performed in solventless conditions with a large excess of water: $H_2O/Si=20$:

1—100 ml of MTEOS (methyltriethoxysilane) are poured in a Schlenk tube

2—180 ml $H_2O$ pH=3.8 (HCl) are added under vigourous stirring

3—The mixture is stirred for 15-16 hours

4—Alcohol is removed under vacuum until the initial volume is obtained

5—the sol is kept at 4° C. until decantation occurs

6—The water phase is removed

7—120-150 ml diethyl ether are added

8—the water phase at the bottom of the Schlenk tube is removed

9—$MgSO_4$ is added to eliminate remaining water molecules

10—$MgSO_4$ is eliminated by filtration

11—Ether is removed under reduced pressure

12—Distilled THF is added

13—The sol is evaporated to the final solid content (40 wt %)

The condensation rate measured by NMR spectroscopy is around 0.8.

Example 2

An organo-silicon sol is prepared according to the procedure described in example 1.

The following platinum based chromophore: trans-di(arylalkynyl)diphosphine platinum(II) based complexes:

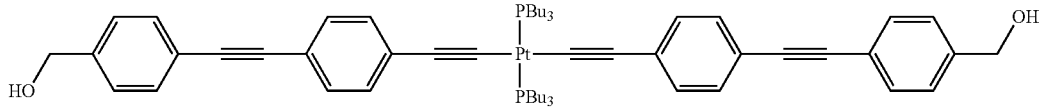

is dissolved (132 mg) in THF and (0.8 mL) added to the sol under moderate heating (45° C.) to increase the solubility. The mixture is stirred for 5 minutes and filtered through a 45 μm filter in a Teflon mould. 45 μL of APTES are added to 1 g of sol of 30% solid content to induce fast condensation of the network. The gel is formed after few minutes. After gelation, the loaded Teflon mould is closed and put in a drier at 45° C. The gel is slowly dried for 48 h at 45° C. and for 48 h at 100° C. Materials with 400 mM concentration (30-40% in mass) are prepared.

Materials were prepared using the same procedure for the following doping agents: tert-butylphenol, surfactants (P123), ionic liquids (Butyl-3-methylimidazolium chloride), lanthanide complexes, 1,4,8,11,15,18,22,25-octabutoxyphtalocyanine, 2,11,20,29-tetra-tert-butyl-2,3-naphatlocyanine, 1-, Pyrromethene597, metal nanoparticles (Au, Ag).

Example 3

An organo-silicon sol is prepared according to the procedure described in example 1 to produce pyrromethene 597 (formula below) doped xerogel.

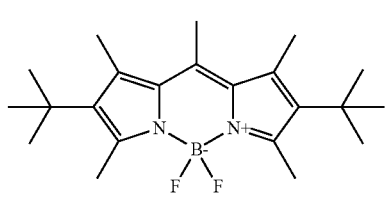

1 g of sol (solid content 30%) is weighed in a Teflon mould.

15 mg of Pyrromethene 597 are then added in the sol. Addition of a small amount of THF (0.3 mL) as well as a mild heating (45° C.) is required to fully dissolve the chromophorpyrromethene 597 molecules.

45 μL of APTES are introduced in the obtained doped sol.

The loaded Teflon mould is closed and put in a drier at 45° C. The gelation occurs several minutes after the mould was introduced in the drier. After 72h drying a transparent, polishable, doped xerogel is obtained.

Example 4

An organo-silicon sol is prepared according to the procedure described in example 1. A solution of 1,4,8,11,15,18,22,25-octabutoxyphtalocyanine in THF (1 mM) is prepared.

1 g of sol (solid content 30%) is weighed in a Teflon mould.
100 µL of the phtalocyanine solution are added with 0.3 mL of distilled THF.
45 µL of APTES are introduced in the obtained doped sol.
The loaded Teflon mould is closed and put in a drier at 45° C. The gelation occurs several minutes after the mould was introduced in the drier. After 48h drying a green, transparent, polishable, doped xerogel is obtained. A doped gel was prepared by using a similar approach except that the APTES was not added before the mould was introduced in the drier. After several days drying a doped xerogel with precipitates was obtained.

The same results were observed in the case of 2,11,20,29-tétra-tert-butyl-2,3-naphatlocyanine.

Example 5

An organo-silicon sol is prepared according to the third variant described in the specification. Acidic water (pH=3.8, HCl) with xH$_2$O/xSi=20 is added (250 mL) into a mixture of MTEOS (110.7 mL) and GLYMO (3-Glycidoxypropyltriethoxysilane) (30.7 mL). The obtained solution is heated for several hours at 100° C. After cooling, the released alcohol and a part of water are removed under reduced pressure. Drying of the sol is performed by using MgSO$_4$ as drying agent. THF is used as final solvent. The solid content of the sol is around 30%. The following platinum based chromophor is used as doping agent:

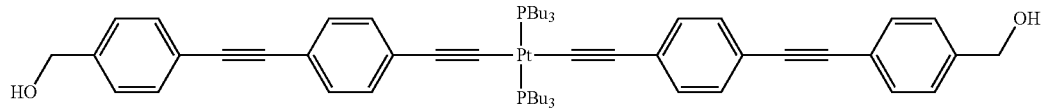

1 g of sol (solid content 30%) is weighed in a Teflon mould.
16.3 mg of chromophor are then added in the sol
Then a mild heating (45° C.) is required to fully dissolve the chromophor molecules.
45 µL of APTES are introduced in the obtained doped sol.
The loaded Teflon mould is closed and put in a drier at 45° C. The gelation occurs several minutes after the mould was introduced in the drier. After 72 h drying a transparent, polishable, doped xerogel is obtained.

The invention claimed is:

1. A hybrid organic-inorganic material constituted by a silica network in which at least one doping agent, representing at least 30% in mass of the material, is included, wherein the hybrid organic-inorganic material is a massive monolith material and the doping agent is not functionalized with siloxane groups and is selected from the group consisting of photochromic agents and optical power limiting agents.

2. The hybrid organic-inorganic material according to claim 1, wherein the doping agent is a platinum(II) complex.

3. The hybrid organic-inorganic material according to claim 2, wherein the doping agent is acetylide.

4. The hybrid organic-inorganic material according to claim 1, wherein the massive monolith material is selected from the group consisting of a xerogel, an aerogel, and a thin film.

5. The hybrid organic-inorganic material according to claim 1, wherein the doping agent is uniformly distributed in the material.

6. The hybrid organic-inorganic material according to claim 1, wherein the doping agent is not aggregated.

7. The hybrid organic-inorganic material according to claim 1, wherein the at least one doping agent represents at least 40% in mass of the hybrid organic-inorganic material.

8. A hybrid organic-inorganic material constituted by a silica network in which at least one doping agent, representing at least 30% in mass of the hybrid organic-inorganic material, is included, the doping agent being selected from the group consisting of photochromic agents and optical power limiting agents, the hybrid organic-inorganic material obtained by the following successive steps:
preparation of a neutral organosilicon sol in at least one organic solvent,
incorporation of the at least one doping agent into the neutral organosiliconsol, and production of a doped sol,
incorporation into the doped sol, of an accelerating agent in order to activate the subsequent gelation of the sol,
condensation of the sol in order to obtain a crosslinked gel, and
drying of the gel and production of a stable doped gel to make the hybrid organic-inorganic material.

9. The hybrid organic-inorganic material according to claim 8, wherein the at least one doping agent represents at least 40% in mass of the hybrid organic-inorganic material.

* * * * *